(12) United States Patent
Mathur et al.

(10) Patent No.: US 10,811,127 B1
(45) Date of Patent: Oct. 20, 2020

(54) AUTOMATING PRESCRIPTION REFILLS USING MACHINE NAVIGATION OF INTERACTIVE VOICE RESPONSE TREES USED BY PHARMACIES

(71) Applicant: Sempre Health, Inc., San Francisco, CA (US)

(72) Inventors: Anurati Mathur, San Francisco, CA (US); Swaraj Banerjee, San Francisco, CA (US); Jason Asare Antwi, Oakland, CA (US); Fadi Almachraki, Oakland, CA (US); Joshua Brian Primas, San Francisco, CA (US)

(73) Assignee: Sempre Health, Inc., San Francisco, CA (US)

( * ) Notice: Subject to any disclaimer, the term of this patent is extended or adjusted under 35 U.S.C. 154(b) by 0 days.

(21) Appl. No.: 16/813,249

(22) Filed: Mar. 9, 2020

(51) Int. Cl.
*G16H 20/10* (2018.01)
*G10L 15/22* (2006.01)
*G10L 15/26* (2006.01)

(52) U.S. Cl.
CPC ............. *G16H 20/10* (2018.01); *G10L 15/22* (2013.01); *G10L 15/26* (2013.01)

(58) Field of Classification Search
CPC ........ G16H 10/60; G16H 20/10; G16H 70/20; G10L 15/22
See application file for complete search history.

(56) References Cited

U.S. PATENT DOCUMENTS

| | | | |
|---|---|---|---|
| 6,680,999 B1* | 1/2004 | Garcia | H04M 3/493 379/88.22 |
| 10,009,467 B1* | 6/2018 | Valiente | H04M 3/5231 |
| 2002/0116270 A1* | 8/2002 | Potiker | G06Q 30/0601 705/14.27 |
| 2006/0149587 A1* | 7/2006 | Hill, Sr. | G06F 19/3456 705/2 |
| 2006/0224414 A1* | 10/2006 | Astrup | G06Q 50/22 705/2 |
| 2009/0043608 A1* | 2/2009 | Nadas | G06Q 10/06311 705/3 |
| 2011/0082705 A1* | 4/2011 | Kobylevsky | G06Q 30/06 705/2 |
| 2013/0272511 A1* | 10/2013 | Bouzid | G06F 8/38 379/88.01 |
| 2015/0350427 A1* | 12/2015 | Benway | H04M 3/493 379/88.01 |
| 2016/0050317 A1* | 2/2016 | Natesan | H04M 3/493 379/88.01 |
| 2016/0198045 A1* | 7/2016 | Kulkarni | H04M 3/4938 379/88.01 |

(Continued)

FOREIGN PATENT DOCUMENTS

WO    WO-03046789 A1 *   6/2003   ............. G06Q 50/22

OTHER PUBLICATIONS

Lee, Haeok, "Interactive Voice Response System (IVRS) in Health Care Services," Nursing Outlook, Nov./Dec. 2003 (Year: 2003).*

(Continued)

*Primary Examiner* — John P Go
(74) *Attorney, Agent, or Firm* — Beyer Law Group LLP (57) ABSTRACT

A system and method for automating the process of renewing prescriptions on behalf of patients using machine navigation of Interactive Voice Response (IVR) trees used for the refilling of prescriptions used by most local pharmacies.

7 Claims, 9 Drawing Sheets

(56) References Cited

U.S. PATENT DOCUMENTS

2016/0292456 A1* 10/2016 Dubey .................... G06F 16/21
2017/0357774 A1* 12/2017 Figg .................... G06F 19/3456

OTHER PUBLICATIONS

YouTube Video webpage and transcript, "Google Duplex: A.I. Assistant Calls Local Businesses to Make Appointments", https://www.youtube.com/watch?v=D5VN56jQMWM, May 8, 2018.
Rasa, "Building Your Own Duplex AI Agent Using Rasa and Twilio", https://blog.rasa.com/building-your-own-duplex-ai-agent-using-rasa-and-twilio/, Jul. 19, 2018.
GetHuman, "Fix Your Customer Service Issues Faster", https://gethuman.com/, various screenshots of a website that was available prior to the filing date of the present application.
Twilio, "Make and Receive Phone Calls With Programmable Voice", https://www.twilio.com/docs/wireless/tutorials/communications-guides/how-to-make-and-receive-phone-calls, Jan. 1, 2019.
CVS Pharmacy, Refill Prescriptions via Text, https://www.cvs.com/mobile-cvs/text-to-refill, screenshot of a webpage that was available prior to the filing date of the present application.
Wit.ai, "Introducing the Refreshed Wit.ai", https://medium.com/wit-ai/introducing-the-refreshed-wit-ai-3a7c603d325a, various screenshots of a website that was available prior to the filing of the present application.

* cited by examiner

TEXT TO DIGIT

| INTENT | ACTION |
| --- | --- |
| refill a prescription press one | PressOne |
| request a refill press one | PressOne |
| enter your telephone number | EnterPhoneNumber |
| enter your ten digit phone number | EnterPhoneNumber |
| last four digits of your phone number | EnterLastFourPhoneNumberDigits |
| last four digits of your telephone number | EnterLastFourPhoneNumberDigits |
| enter your prescription number | EnterRxNumber |
| enter the prescription number | EnterRxNumber |
| enter the seven digit refill number | EnterRxNumber |
| letters of your last name press one | PressOne |
| if this is correct press one | PressOne |
| to confirm press seven | PressSeven |
| if you are finished press three | PressThree |
| for no other refills press two | PressTwo |
| finished entering prescriptions press three | PressThree |
| finished with your prescription refill press three | PressThree |
| prescription has been filled | PressThree |
| if not press two | PressTwo |
| your request has been submitted | DoNothing |
| pick up your prescription order press one | PressOne |
| entered one prescription refill request | PressZero |
| confirm that you will be picking up your order press one | PressOne |
| hear an estimated pickup time | PressTwo |
| got that right | PressOne |
| to accept this time | PressOne |
| like to pick it up then press one | PressOne |
| no refills remaining on your prescription | Wait |
| pharmacy to contact your doctor press one | PressOne |
| contact your doctor for additional refills | PressOne |
| records indicate that you have one or more prescriptions | PressThree |
| press one now otherwise press three now | PressThree |
| to leave a voice message with this request | PressZero |
| leave a message along with your order | PressTwo |
| if you find it necessary to speak to a member | PressOne |
| order is complete press pound | DoNothing |
| was filled and is ready for pickup | HangUp |
| goodbye | HangUp |
| thank you for your order to return | HangUp |

FIG. 6

TEXT TO VOICE

| INTENT | ACTION |
|---|---|
| what can I do for you | SayNeedRefill |
| how can I help you | SayNeedRefill |
| i need a refill | SayNeedRefill |
| what's the rx number | SayRxNumber |
| what is the rx number | SayRxNumber |
| say or enter the prescription number | SayRxNumber |
| would you like us to contact them for you | SayYes |
| did i get it | SayYes |
| right | SayYes |
| is that right | SayYes |
| just a second while i look it up | SayYes |
| do you need it refilled sooner | SayNo |
| do you want to refill another | SayNo |
| another prescription you'd like to refill | SayNo |
| another prescription you would loike to refill | SayNo |
| have another presciption to refill today | SayNo |
| would you like to put it on automatic refill | SayNo |
| prescription on automatic refill press one on your telephone | PressTwo |
| prescriptions in three month supply | SayNo |
| when would you like to pick that up | SayToday |
| what time | Say5PM |
| if that time works for you | SayConfirmIt |
| just say confirm it | SayConfirmIt |
| like me to repeat that | SayNo |
| hear that information again | PressTwo |
| receiving a flue shot when you come | SayNo |
| generic available | SayNo |
| you like the generic | SayNo |
| may hang up now | HangUp |
| hang up | HangUp |

FIG. 7

AUTOMATING PRESCRIPTION REFILLS USING MACHINE NAVIGATION OF INTERACTIVE VOICE RESPONSE TREES USED BY PHARMACIES

FIELD OF THE INVENTION

The present application is directed to refilling medical prescriptions for patients, and more particularly, to automating the process of refilling prescriptions on behalf of patients using machine navigation of telephone Interactive Voice Response (IVR) trees used by most local pharmacies for prescription refills.

DESCRIPTION OF RELATED ART

The field of medicine has drastically changed in recent years. More and more pharmaceutical drugs are being developed and used to treat a wide variety of disorders, conditions and diseases. For instance, statin drugs are widely prescribed for patients with high levels of blood cholesterol. By taking statins, the risk of heart attacks and strokes is reduced. Immuno-suppressant drugs, which reduce the strength of the immune system of a patient, are used to treat a number of autoimmune disorders, such as lupus, psoriasis and rheumatoid arthritis. Insulin drugs are now widely used to treat diabetic patients. The above are just a few of the many examples where pharmaceutical drugs are being used to save lives and improve the quality of life. Such advances in healthcare will only continue into the future as an ever expanding variety of prescription drugs are developed and made available to patients with a wide variety of disorders, conditions and diseases.

The typical model for the distribution of prescription drugs is through a network of doctors, health insurance providers, and local pharmacies. A patient will visit a doctor for diagnosis for a disorder, condition or disease. For treatment, the doctor will often prescribe a pharmaceutical drug and make arrangements for the patient to pick up the prescription at their local pharmacy. At the pharmacy, the patient provides their insurance information to the pharmacist. In response, the pharmacy initiates an electronic transaction with the health insurance provider of the patent. During the transaction, the pharmacy uses the cost of the prescription and the amount the insurance provider will cover to determine the remaining co-payment amount by the patient. For example, if the cost of the prescription is $500, and the insurance provider covers 90% or $450, then the co-pay amount is $50. When the prescription is purchased, the pharmacy invoices the health insurance provider for the $450 and receives the $50 co-pay from the patient, completing the transaction. On occasion, a patient may have secondary insurance. In which case, the above process is repeated and the secondary provider pays some or all of the outstanding co-pay and the remaining amount is paid by the patient.

For many chronic disorders, conditions and diseases, a doctor will often prescribe that a medication be refilled either indefinitely or for a fixed number of times (e.g. 4, 5 or 6 refills). Patients often do not refill their prescriptions for a number of reasons. When a current supply of the prescription is about to run out, the burden is typically on the patient (or a spouse, family member, friend or caregiver) to call the local pharmacy and request the refill. Very often, however, the request is not timely made if at all. Patients often forget, or are too busy, to call their local pharmacy and ask for the refill. As a result, prescriptions are often refilled late, or not refilled at all, and patients do not take their medications as prescribed. The percentage of prescriptions not refilled has been estimated to be approximately thirty percent.

Patient non-adherence to their prescription drug protocols can have significant ramifications for patients, health care providers and pharmaceutical companies alike.

In the case of patients, their disorders, conditions and/or diseases may worsen. The failure to take medication may possibly lead to a decrease in the quality of life, an increase in unplanned hospital and/or medical care visits, or in extreme situations, premature death.

For health insurance providers, non-adherence may lead to significant financial consequences. If patients do not take their medications, the risk of non-planned medical events may significantly increase. If a patient does strictly adhere to taking a prescribed statin drug for example, the risk of heart attack and/or stroke is significantly increased. If a patient in fact suffers a heart attack or stroke, expenditures by the health insurance provider will likely be significantly higher than the cost of the drug, particularly if hospitalization, surgery, and/or rehabilitation for the patient are required.

Pharmaceutical companies lose significant revenue if prescriptions are not refilled. If a patient refills a $500 prescription every month, then the annual revenue for the pharmaceutical company from that one patient is $6000. But if the patient refills the prescription only six times during the course of a year, then the revenue for the pharmaceutical company is only $3000. In the United States, nearly half the population is taking a prescription drug. With approximately thirty percent of these prescriptions not refilled, the total loss of revenue for the pharmaceutical industry as a whole can be in the range of billions of dollars.

An easier, more convenient way to request refills of prescriptions is therefore needed.

SUMMARY

The present application is directed at a system and method for automating the process of renewing prescriptions on behalf of patients using machine navigation of telephone Interactive Voice Response (IVR) trees used by most local pharmacies for prescription refills.

In one non-exclusive embodiment, patient refills are tracked and patients receive timely electronic message reminders requesting if they wish to have their prescriptions refilled. If a positive response is received, steps for automating the process for refilling the prescription are taken. If no positive response is received, then one or more additional reminders may be sent.

In a non-exclusive embodiment, automating the process of prescription refills involves machine navigation of a telephone IVR tree, which now are commonly used by most local pharmacies. The IVR is navigated by connecting to the IVR tree via a phone call, converting a phrase uttered by the IVR into a text string, classifying an intent of the phrase from the text string and responding to the phrase uttered by the IVR with an action that corresponds to the classified intent. After an action is taken, the above-process is repeated until the request to refill the prescription is complete. At a minimum, a successful navigation of an IVR tree for a prescription refill requires at least the entering of some identifying information associated with the patient and a prescription number, although other information may be required as well.

In non-exclusive embodiments, an intent table is used for classifying the intent of the phrases uttered by the IVR tree. The intent table typically includes (a) multiple intent classifications, (b) one or more expressions for each of the multiple intent classifications and (c) a defined action for each of the multiple intent classifications.

During operation, the text string for an utterance made by the IVR tree is compared to the one or more expressions for each of the multiple intent classifications. A probability score is assigned to each of the one or more expressions. The intent of the text string is then classified from the expression having the highest probability score based on the comparisons. The defined action for the classification is then entered to the IVR. In various embodiments, the action can be entered in the form of either machine generated voice or frequency tones (DTMF).

In preferred, but by no means exclusive embodiments, correspondence with the patients is conducted via text messaging. Emails, phone calls and other means of communication or correspondence can also be used as well.

The above-described system and method for automating the refill of prescriptions offers a number of advantages. Texting reminders, and receiving text replies, is an extremely easy form of communication since text messaging is now near ubiquitous, provides communications immediately, and is near "frictionless" for patients to use. Also, machine-to-machine navigation of IVRs eliminates the burden on the patient, or some other human, to call in and refill prescriptions. The combination of these two advantages results in a significantly higher rate prescription refills.

By using text messaging and automating the refill process, patients adhere to their prescription protocols at a higher rate, improving their health and quality of life. Insurance health providers benefit by seeing fewer unplanned medical visits to doctor offices, clinics and hospitals, saving money. Pharmaceutical companies sell more prescriptions, which increases revenue and improves their bottom line.

BRIEF DESCRIPTION OF THE DRAWINGS

The present application and the advantages thereof, may best be understood by reference to the following description taken in conjunction with the accompanying drawings in which:

FIG. 6 and FIG. 7 are different examples of intent classification and action tables used during navigation of IVR trees in accordance with non-exclusive embodiments of the invention.

In the drawings, like reference numerals are sometimes used to designate like structural elements. It should also be appreciated that the depictions in the Figures are diagrammatic and not necessarily to scale.

DETAILED DESCRIPTION

The present application will now be described in detail with reference to a few non-exclusive embodiments thereof as illustrated in the accompanying drawings. In the following description, numerous specific details are set forth in order to provide a thorough understanding of the present disclosure. It will be apparent, however, to one skilled in the art, that the present disclosure may be practiced without some or all of these specific details. In other instances, well known process steps and/or structures have not been described in detail in order to not unnecessarily obscure the present disclosure.

Prescription Medical Fulfillment System

Figure 1:
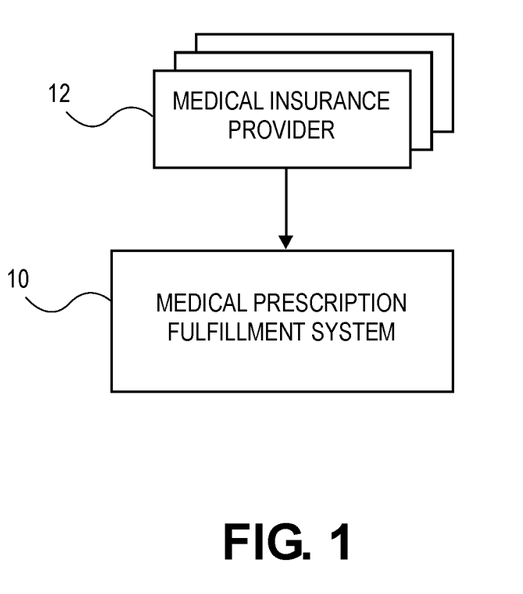
FIG. 1 illustrates a diagram of a system for automatically refilling prescriptions for patients in accordance with a non-exclusive embodiment of the invention.

Referring to FIG. 1, a diagram of a medical prescription fulfillment system 10 for automating the process of refilling prescription process is illustrated. The medical prescription fulfillment system 10 is arranged to receive patient data from any of a number of partner sources, including but not limited to health insurance providers 12. As previously noted, patient adherence to the prescription protocols benefits health insurance providers since patients that timely take their medications are likely to need few unplanned medical visits to doctors, clinics and hospitals. Accordingly health insurance providers, such as Blue Cross Blue Shield, Cigna Health, etc., have a strong financial motivation to have their covered patients enroll in and participate in the services provided by the medical prescription fulfillment system 10.

Once the patient information is received, the medical prescription fulfillment system 10 maintains the data in a uniform format. By accessing the database and running certain algorithms, the medical prescription fulfillment system 10 is capable of (1) tracking when prescriptions for individual patients are due for a refill, (2) timely sending correspondence to the individual patients requesting if they would like to have their prescription refilled, (3) sending out multiple reminders if needed, (4) automating the refill process by machine navigating an Interactive Voice Response (IVR) tree used by the local pharmacy of the patient and (4) notifying the patient when their refill will be ready for pickup.

Figure 2:
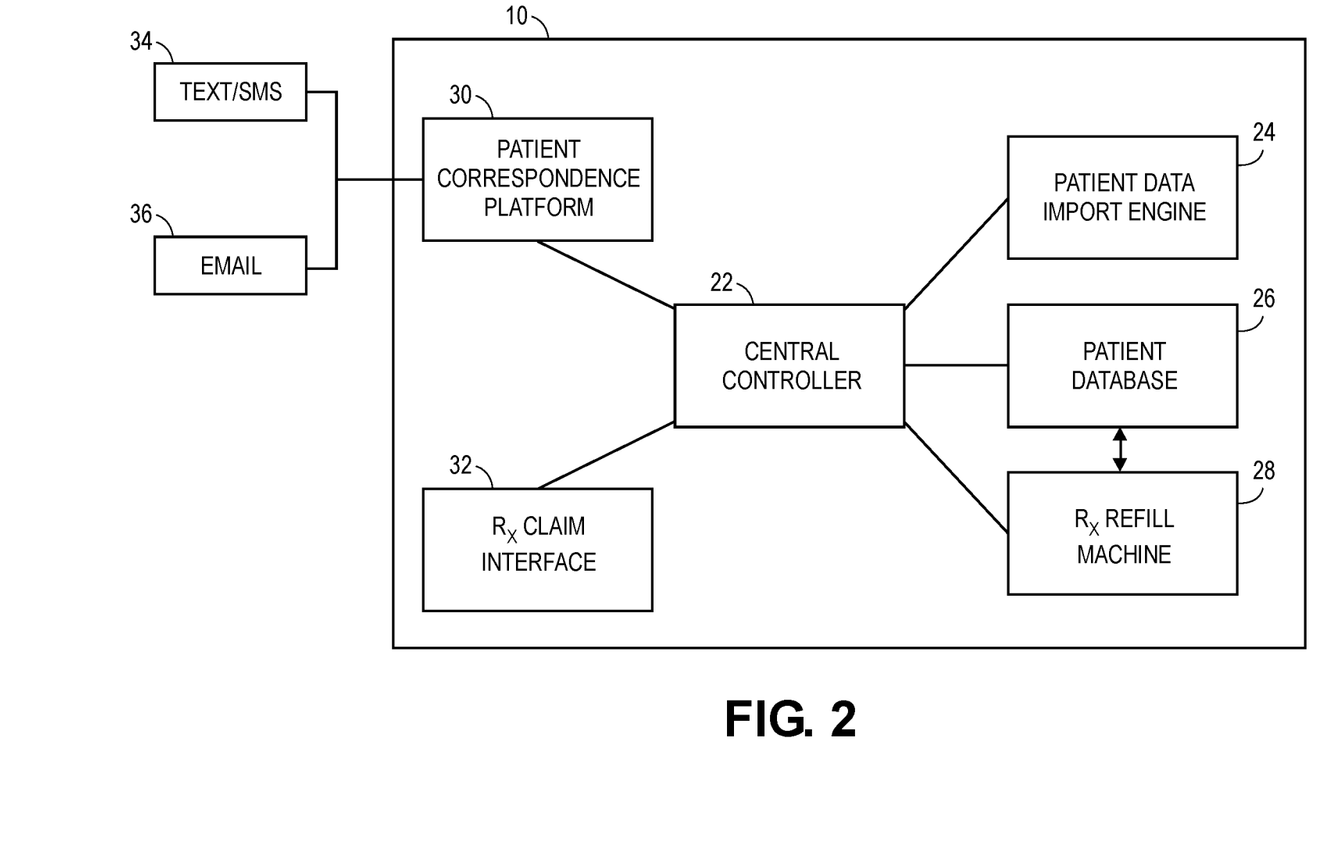
FIG. 2 is a block diagram illustrating a medical prescription fulfillment system for implementing the automatic refill of prescriptions for patients in accordance with a non-exclusive embodiment of the invention.

Referring to FIG. 2, a block diagram of the medical prescription fulfillment system 10 is illustrated. The medical prescription fulfillment system 10 includes a central controller 22, a patient data import engine 24, a patient database 26, a prescription (Rx) refill machine 28, a patient correspondence platform 30 and prescription claim interface 32.

The central controller 22 supervises most of the operations performed by the medical prescription fulfillment system 10. These operations include, but are not limited to, receiving raw patient data from health insurance provider(s) 12, managing the patient data import engine 24, which converts the raw patient data into a uniform format of patient records, storing in the patient database 26 the patient records in the uniform format, coordinating with the prescription (Rx) refill machine 28 for submitting prescription refill requests on behalf of patients, managing the patient correspondence platform 30 for generating and receiving correspondence with patients, and coordinating with the Rx claim interface 32 for receiving confirmations for insurance claims for refilled prescriptions, which typically signifies that the refill requests made by the Rx refill machine have been successful.

The patient data received from different sources, such as from various health insurance providers 12, is typically in different formats. The patient import engine 24 is used to transform the patient data into a uniform format regardless of how the data was received. The individual patient records, in the uniform format, are then stored in the patient database 26.

The patient database 26 is used for storing patient records in the uniform format. The uniform format generally organizes the data for individual patients into records that include (a) healthcare insurance provider specific data including the name of carrier, type of plan, group number, subscriber, etc.), (b) patient specific data including name, address, home phone, cell phone, date of birth, etc.), (c) local pharmacy specific data such as the name of the pharmacy used by the patient, National Provider Identifier or "NPI", telephone number, address, etc.) and prescription drug specific data such as for each prescription drug, (d) a drug identifier or ID, (e) the days supply of the prescription (e.g., 7 days, 30 days, 60 days, etc.), (f) the number of times the prescription may be refilled and (g) optionally the co-pay benefit amount provided by the health insurance provider. It should be understood that the patient records as listed herein is merely exemplary. Other patient records may be included in the patient database 26 as well.

The prescription (Rx) refill machine 28 is essentially a robot that is capable of automatically traversing the Interactive Voice Response (IVR) trees typically used now by most pharmacies for prescription refills. As described in detail below, the prescription (Rx) refill machine 28 is capable of calling the pharmacy of a patient, navigating the IVR, and placing a request for a prescription to be refilled on behalf of a patient.

The patient correspondence platform 30 provides a two-way interface between the central controller 12 and any number of known communication platforms, such as text or SMS messaging platforms 34 or email platforms 36. The central controller 22 determines when timely correspondence should be sent to patients. Such correspondence may include an initial contact requesting if a patient would like to have their prescription refilled and any needed follow up reminders. Once the central controller 22 formulates the content of a message for a patient, the patient correspondence platform 30 coordinates with either the text/SMS platform 34 or the email platform 36 and coordinates the sending of the electronic message to the patient. If the patient responds, then the reply is provided to the central controller 22 via the patient correspondence platform 30. The central controller is responsible for coordinating activities in response to the reply. For instance if a patient provides a positive response that they would like to have their prescription refilled, then the central controller 22 activates the prescription refill machine 28 to call the local pharmacy of the patient and enter the refill request.

The prescription claim interface 32 is provided to receive some type of notification to the central controller that claim for payment for the refill of the prescription has been made. Typically, when a prescription is filled by a local pharmacy, they will electronically invoice the health insurance provider of the patient. For example if a prescription cost $100, and the insurance provider covers $80.00, then the insurance company is invoiced the covered amount while the patient is required to pay the co-pay remainder amount, which in this case is $20.00. Thus, such a notification can be used as an indicator that the request for the refill was successful. In response, the central controller 22 can arrange through the patient correspondence platform 30 to inform the patient, typically in the form of a text, that the refill request is or will be ready for pickup.

In various embodiments, the notice may be generated by one of several parties, including the health insurance provider 12 of the patient.

On-Boarding Patient Data

The medical prescription fulfillment system 10 ideally maintains the records of potentially thousands upon thousands of patients in a uniform format in the patient database 26. The various partner health insurance providers 12, however, will each typically maintain their patient records in different formats and/or databases. The challenge, therefore, is to extract raw data received from these various sources of patient data and transform the raw data into a uniform format of patient records that is maintained in the patient database 26.

Figure 3A:
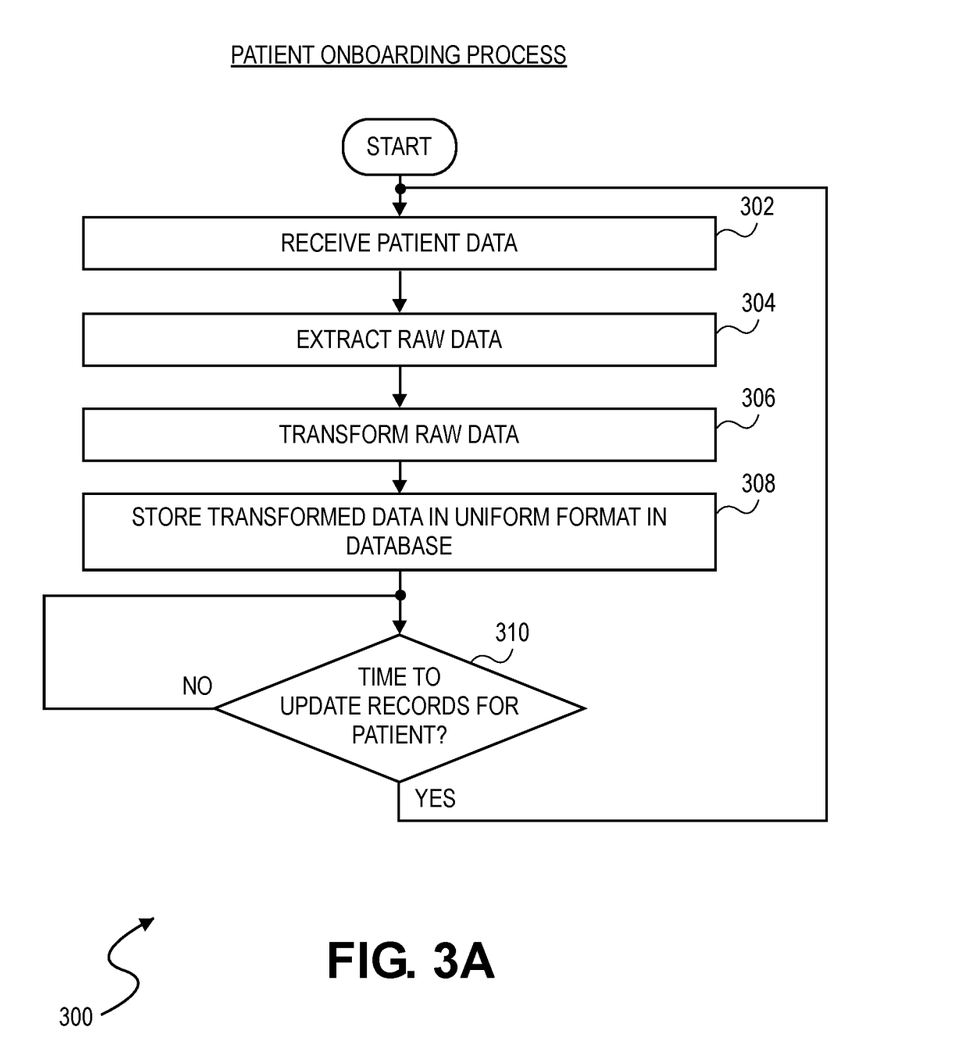
FIG. 3A illustrates various steps for on-boarding patient data in accordance with non-exclusive embodiments of the invention.

Referring to FIG. 3A, a flow diagram 300 illustrating the steps for on-boarding and transforming patient records into a uniform format is illustrated.

In the initial step 302, patient records containing raw data is received in any of a number of different formats.

In step 304, the raw data is extracted from the received patient records.

In step 306, the patient data import engine 24 transforms the raw data into a uniform format.

In step 308, the transformed data is stored in the uniform format in the patient database 26.

In decision step 310, it is determined if the patient records should be updated. With the passage of time, some of the data maintained in the database 26 may become stale or out of date. For example, new patients may join with a participating health insurance provider 12 or others may leave. Or the medical situation for a given patient may change. A doctor may change a prescription from one drug to another, prescribe multiple new drugs, or take a patient off a previously prescribed drug. For any of these reasons, the patient records maintained in the database 26 may need to be updated from time to time. Whenever a need arises to update the records of a patient, then steps 302 through 308 are repeated. In this way, the patient database maintains up-to-date records for participating patients on an ongoing basis.

The updating of patient records typically involves coordination with partner health insurance providers 12. In a non-exclusive embodiment, a notice is sent to the medical prescription fulfillment system 10 whenever changes in the records of a patient are made in the database of a partner health insurance provider 12. In response to the notice, a data update process is initiated. In this update process, the updated patient records are uploaded to the patient data import engine 24, transformed by the data import engine 24 and storage in the patient database 26. In this manner, the patient database is kept up to date for individual patients.

Figure 3B:
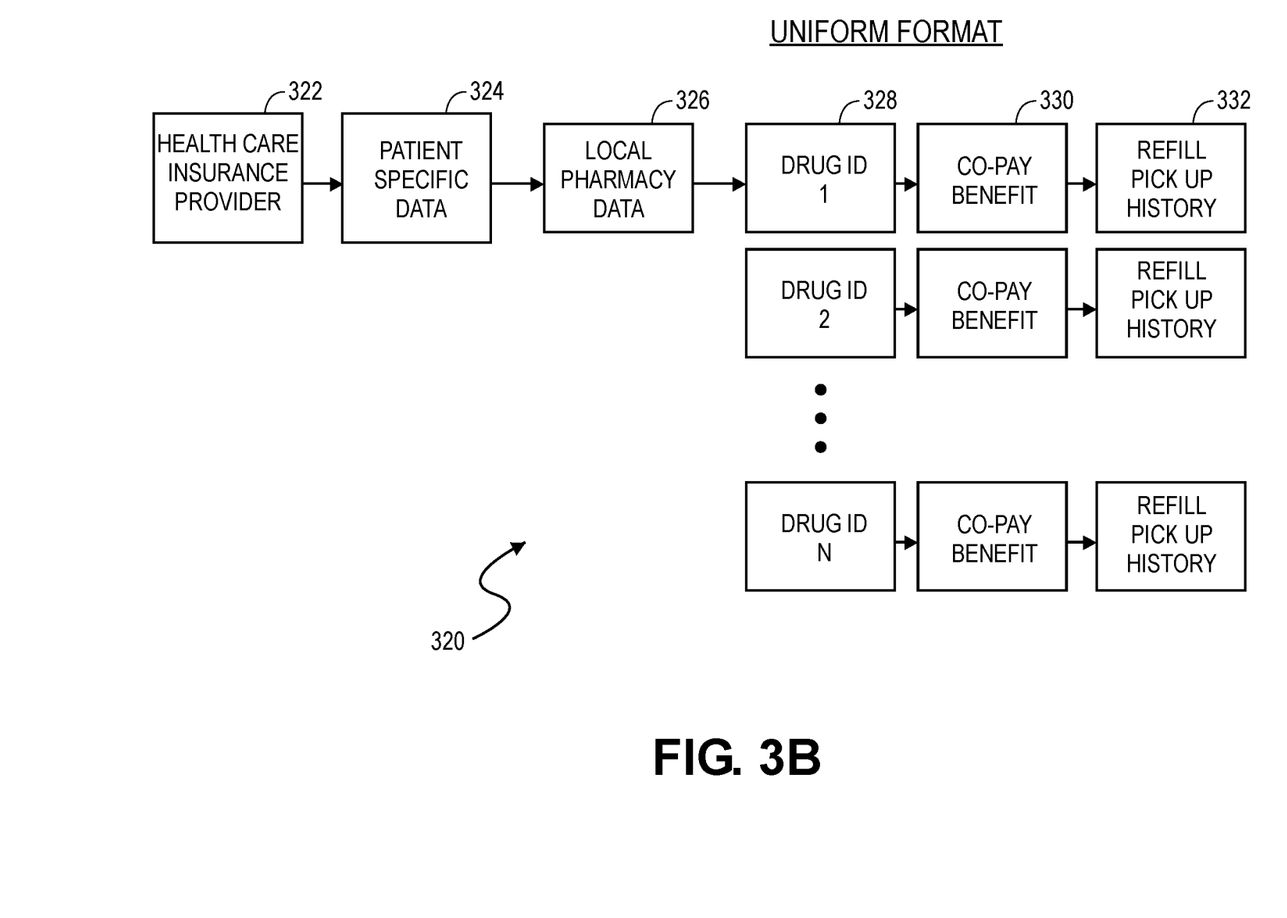
FIG. 3B illustrates the storage of the patient data in a uniform format in accordance with non-exclusive embodiments of the invention.

Referring to FIG. 3B, an exemplary patient record 320 in a uniform format is illustrated. The uniform format includes a number of records, including:

Health care insurance provider information 322 such as a name of the insurance provider, plan name, plan code, effective date, end date, etc.;

Patient specific data 324, such as name, member ID, date of birth, address, phone number, cell, number, email address, etc.;

Patient pharmacy data 326 such name, address, the NPI, telephone number, etc. In the United States, each pharmacy is assigned a unique NPI;

Prescription drug ID information 328 including a drug identifier ID, name of drug, branded drug or generic drug, day supply of prescriptions, number of permitted refills, etc.;

Co-pay benefit details 330 such as the co-pay amount; and

The refill pickup history 332 includes information such as the number of times the prescription was refilled or refill dates.

In various alternative embodiments, the extracted raw data received from participating health insurance provider(s) can be transformed into just about any suitable unified format. As such, the particular format shown is merely exemplary and may widely vary.

Prescription ($R_x$) Refills

The timely pickup of refill prescriptions by patients may not occur for a number of reasons. Patients may forget and realize that they need a refill only after they have run out of their current prescription. Or patients may not have the time to call their local pharmacy to request a refill.

In a non-exclusive embodiment, the medical prescription fulfillment system 10 can be configured to at least partially automate the refilling of prescriptions on behalf of patients, making the process near "frictionless".

Figure 4A:
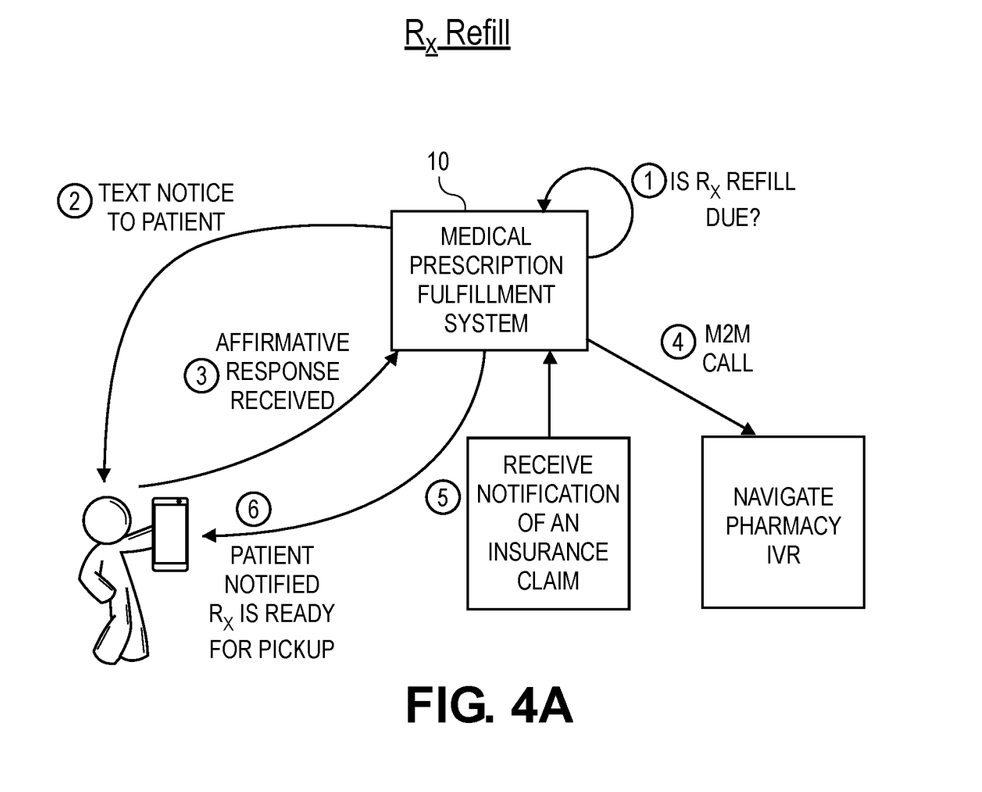
FIG. 4A is an illustration depicting the steps for automating prescription refills on behalf of a patient in accordance with a non-exclusive embodiment of the invention.

As illustrated in FIG. 4A, this process involves the steps of (1) tracking for patients when their prescription refills are due, (2) notifying the patients, preferably by text, when a prescription is due, (3) receiving a reply text from the patient requesting their prescription be refilled, (4) automating the refill request with the local pharmacy of the patient with a Machine-to-Machine (M2M) call placed by the Rx refill machine 28, (5) receiving a notification that an insurance claim for the refill was submitted and (6) notifying the patient, preferably by another text message, when the prescription will be ready for pickup. By using text messaging and M2M calls, the refill process is significantly simplified and is less burdensome for patients. As a result, the timely refill of prescriptions is likely to occur more often.

Figure 4B:
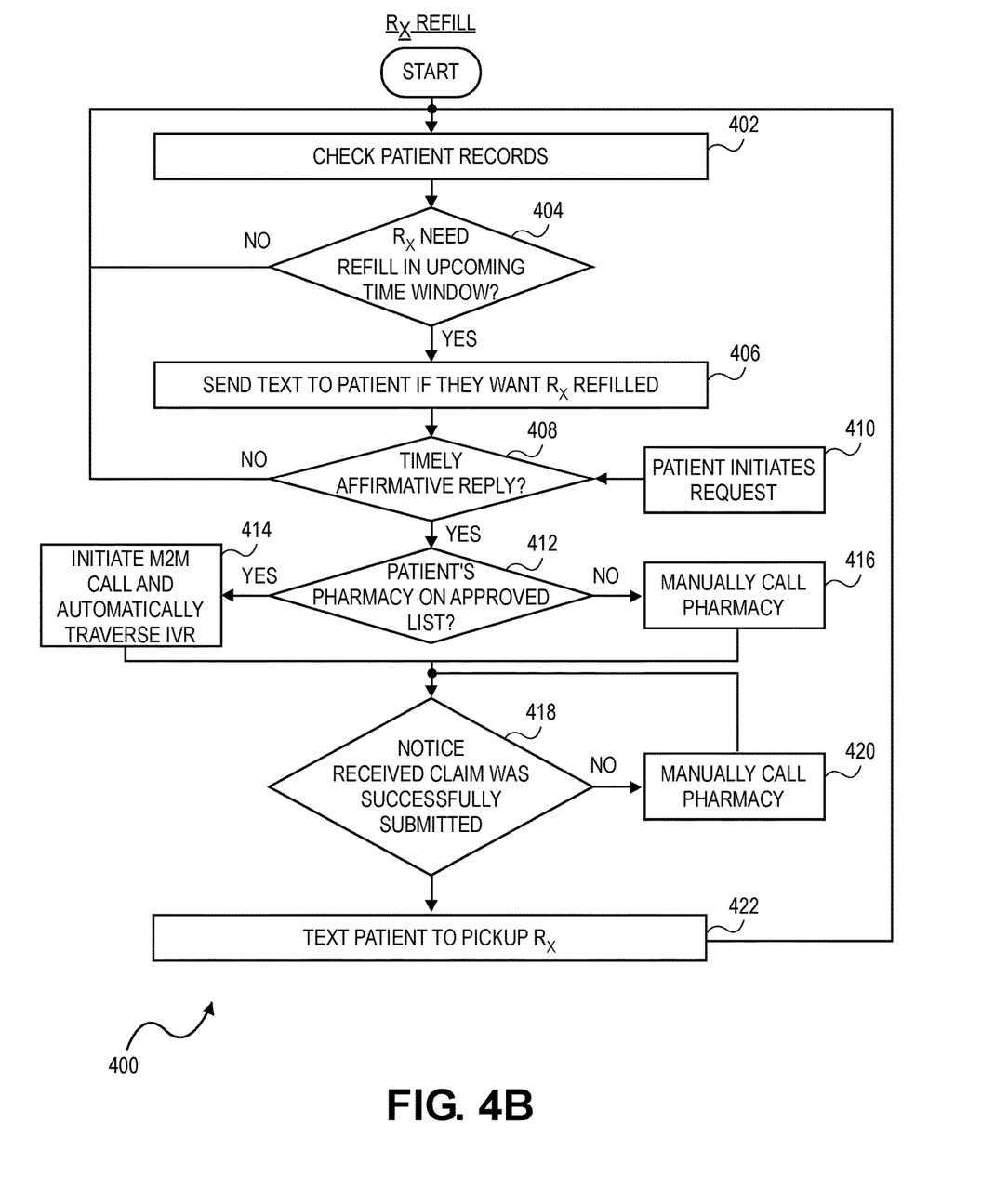
FIG. 4B is a flow diagram illustrating steps for automating prescription refills using text messaging and machine-to-machine calls in accordance with a non-exclusive embodiment of the invention.

Referring to FIG. 4B, a flow diagram 400 illustrating steps for automating prescription refills using the Rx refill machine 28 is illustrated.

In the initial step 402, the records of a patient in the database 28 are periodically checked. The interval in which the records of the patient are checked may widely vary. For instance, the records may be checked on an hourly, daily, weekly, bi-weekly or on a monthly basis. It should be understood that these time intervals are merely exemplary and should not be construed as limiting in any regard. On the contrary, any time interval may be used, including those that are more or less frequent than mentioned herein.

In decision step 404, it is determined if the patient has a prescription refill due in an upcoming time window. As previously noted, the records of the patient maintained in the database 28 contain a wealth of useful information, including drug identifiers or IDs, refill pickup history, local pharmacy information including the NPI, etc. Using this information, it can readily be determined (1) the last time the prescription was filled, (2) the day supply for the current prescription, (3) the estimated supply of the current prescription remaining and (4) the number of remaining refills that are permitted. For example if the day a recurring 30-day prescription was last picked is known, the remaining supply can be readily estimated from the number of days that have passed and the number of days that remain before the supply runs out. With this information, the central controller 22 can make a decision when to send out a text reminder to the patient. The time window defined by the central controller is generally selected to provide the patient with adequate time in which to refill their prescription before an existing prescription runs out, such as five or ten days. Again, it should be understood that any specific time windows mentioned herein is merely exemplary. Different time windows that are either shorter or longer may be used.

If no prescription is due for a refill within the time window, then steps 402 and 404 are repeated indefinitely until a refill for a prescription falls within the time window.

When a prescription is due for a refill within the time window, a text message is sent to the patient as provided in step 406. The content of the text message typically asks if the patient wishes to have their prescription refilled. For instance, a message may read:

"Mary, the refill for your prescription is due February 21$^{st}$. Would you like to have the prescription refilled? Reply 'R' if you'd like us to submit it for you."

While the exact wording may vary, the intent of the text is to notify the patient of the upcoming refill date and elicit from the patient a reply text if they wish to have their prescription refilled.

If multiple refills are due, then typically multiple text messages are sent, one for each prescription. In alternative embodiments, a single text however can be used for multiple prescriptions.

In decision step 408, it is determined if the patient timely replied by text with an affirmative response. Examples of affirmative text replies may be "yes", 'refill", or simply "r", short for refill. Timely means that the response was sent within a reasonable period of time after the patient received the original text. For instance, if the refill date is five days away, then a timely response may be anytime within the five day period or even a few days after. But if an affirmative reply message is sent two weeks after the prescription should have been refilled, then the reply may optionally be ignored or discarded.

The use of text messaging to refill prescriptions offers a number of advantages, all of which are likely to lead to a higher refill rate.

Text messaging is now near ubiquitous. A patient can receive a text, and with virtually no effort, can promptly reply in the affirmative. Texting thus offers an easy way to remind patients of their prescription refills and a near effortless way for them to respond.

Also, texting offers the advantage of easily generating one or more follow up reminders if needed. If a patient does not respond to an initial text for a refill, then one or more reminders can be sent up to or even beyond the due date for refilling the prescription.

In step 410, it is determined if a patient has initiated their own request to refill a prescription without first receiving a text. Mary, in the previous example, may simply text "Refill myprescription" or more simply "refill" or "r" on her own, without prompting from an incoming text. Her text will be processed in a similar manner, resulting in the automated refilling of her prescription.

In decision step 412, it is determined if the pharmacy of a patient is on an "approved" list or not. Most pharmacies today, including the large pharmacy chains such as CVS or Walgreens, use IVR trees for handling the refilling of prescriptions. Other pharmacies, however, may still have a person answer the phone and manually process a refill request. As a general rule, the pharmacies that use IVRs are considered "approved", while those that do not are deemed as not approved.

In step 414, if the pharmacy is approved, a machine-to-machine ("M2M") call is initiated by the Rx refill machine 28 with the IVR. Each pharmacy in the United States is assigned a unique National Provider Identifier (NPI) number. Each NPI has an associated telephone number. With the telephone number known, the Rx refill machine 28 initiates a call, navigates the IVR tree, requesting the refill on behalf of the patient. Most pharmacies typically require at least two pieces of information to process a refill, including a prescription number and some type of identifying information associated with the patient, such as a name, a date of birth, a telephone number, etc., or a combination thereof. This information is typically provided in the records for the patient maintained in the database 28. Once the required information is accessed from the database 28 and provided by the Rx refill machine 28, the pharmacy has sufficient information to go ahead and process the refill.

In step 416, if the pharmacy is not approved, then a manual phone call is placed by a person within the medical prescription fulfillment system 10 to the local pharmacy of the patient. During the phone call, a request for the refill of the prescription of the patient is made by providing the prescription number and the required patient identification information, which is accessed from the database 28.

In decision step 418, it is determined if a notice has been received by the prescription claim interface 32 that the local pharmacy has submitted a claim for at least partial reimbursement for the prescription drug. As previously described, a pharmacy will typically first electronically "ping" the health insurance provider 12 of the patient, learn the coverage amount and then (1) generate an invoice for the covered amount and (2) request the patient pay the remaining co-pay amount when the prescription is picked up. A notice received from the health insurance provider 12, or directly submitted to the medical fulfillment system 10 serves as a highly a reliable indicator that the request by the Rx refill machine 28 was in fact successful. Thus, by arranging to receive a notification that such an insurance claim was made, the central controller 22 can confidently generate a message via the patient correspondence platform 30 for the patient indicating the prescription is or will be ready for pickup. On the other hand if no notice of a claim is received in the reasonable period of time, then it is assumed that the refill request was not successful.

As a general rule, a reasonable time period to wait for the notice of the claim is adequately long to provide the local pharmacy enough time to physically refill the prescription and have it ready for pickup. In one non-exclusive embodiment, the reasonable time period is approximately two days. Within this time period, the pharmacy typically has more than sufficient time to physically fill the prescription and have it waiting for pickup. If, on the other hand, the medical prescription fulfillment system 10 is not billed within the two day period, then an assumption is made that a failure has occurred. It should be understood that the reasonable time period may widely vary. Periods of longer than two days, such as three or four days, may be used as the reasonable time period in some situations, whereas periods of less than two days may be used in other situations.

In step 420, a manual call is placed with the pharmacy if a determination is made that the refill request was not successful. The calling person will either navigate the IVR or speak to another person at the pharmacy. Either way, the manual call is used to request that the prescription be refilled or confirm that the previous attempt by the Rx refill machine 28 was in fact successful.

In step 422, the patient is texted with a message indicating that their refill is ready for pickup at their pharmacy.

The above steps are intended to be repeated. Whenever a patient has a refill for a prescription due within the predetermined time window, the steps 402 through 422 are repeated. This way a patient can have their prescriptions refilled indefinitely, provided they do not exceed their maximum number of permitted refills. In the case of the latter, the patient is typically required to consult with their doctor to have the prescription renewed and/or changed. Assuming the prescription is renewed or a new prescription is prescribed, then the above-described refill system and method can be used again by the patient.

Machine to Machine (M2M) Calls

As previously noted, step 414 involves a M2M call where the Rx refill machine 28 places a call with a local pharmacy and navigates its IVR tree when requesting a prescription refill for a patient. This process typically involves a back-and-forth dialog where the IVR utters a phase prompting the Rx refill machine 28 to enter a required piece of information. Once the piece of information is entered, then the IVR utters another phrase prompting the Rx refill machine 28 to enter another piece of information. This cycle is typically repeated a number times until the tree is successfully navigated and all the information needed to refill the prescription has been entered.

In the Table I below, an exemplary M2M dialog between the IVR of a fulfilling pharmacy and the Rx refill machine 28 during a call to refill a prescription is shown.

TABLE I

| IVR | Rx Refill Machine Action |
| --- | --- |
| Please enter 1 to speak to a person or 2 to refill a prescription. | Action: Say "2" |
| Enter name of patient | Say "Mary Smith" |
| Enter date of birth | Say "Jan. 15, 1948" |
| Enter telephone number of patient | Say "415 751 8853" |
| Enter Rx number | Say "947321" |
| When would you like to pick up the prescription | Say "Tomorrow" |
| Thank you. The prescription will be ready for pick up tomorrow, Dec. 15, 2019, at 9 AM. | Hang up |

Figure 5:
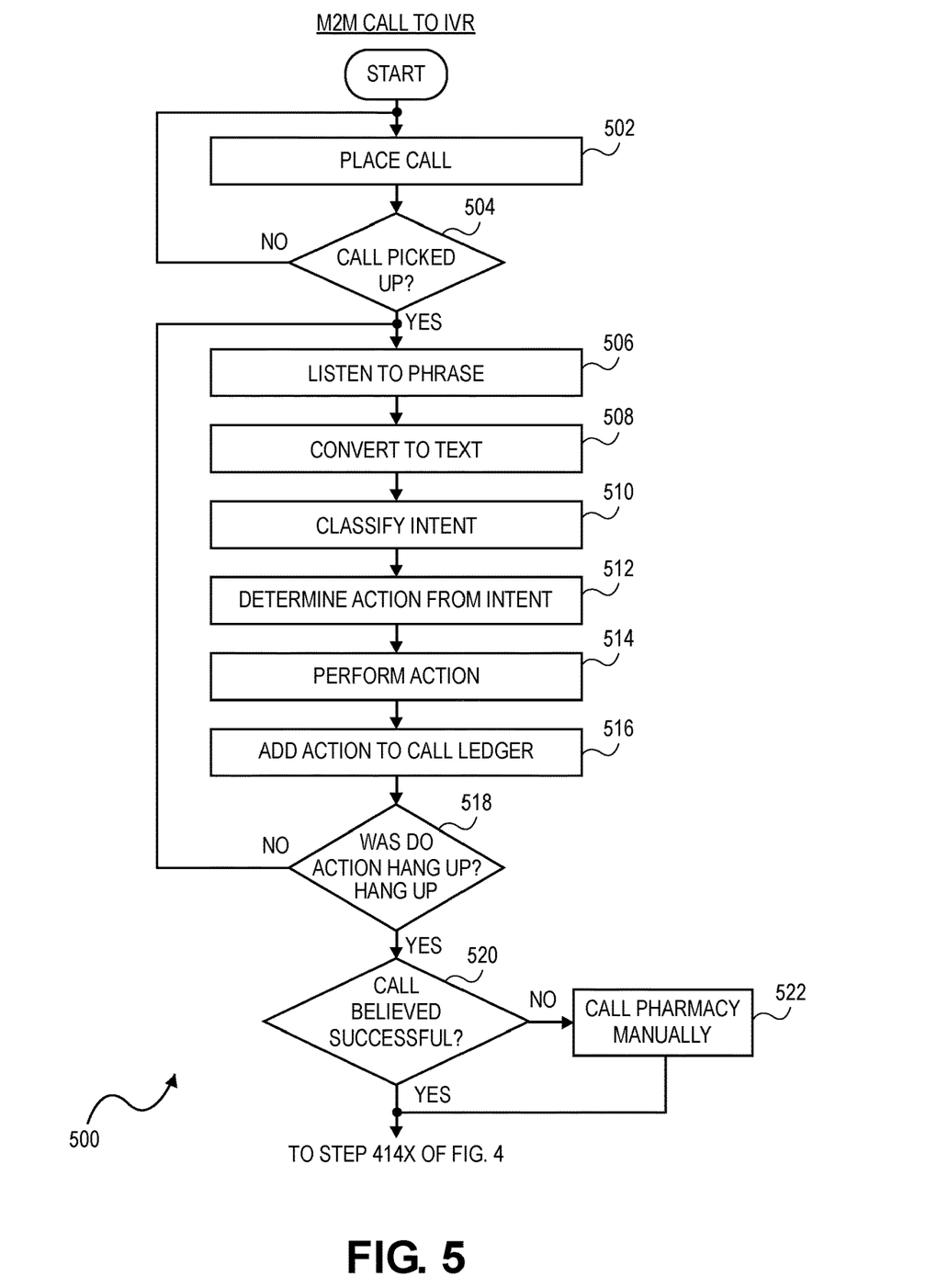
FIG. 5 is a flow diagram illustrating steps for machine navigation of an Interactive Voice Response (IVR) tree for calling in the refill of a prescription in accordance with non-exclusive embodiments of the invention.

Referring FIG. 5, a flow diagram 500 illustrating the steps performed by the Rx refill machine 28 when navigating a call with an IVR tree is illustrated.

In the initial step 502, the Rx refill machine 28 initiates a call with the local pharmacy. As noted above, the Rx refill machine 28 knows the telephone number to use from the NPI number retrieved from the records of the patient from the database 28.

In step 504, the Rx refill machine 28 determines if the call was picked up and a successful connection with the IVR tree has been made. If not, control is returned to step 502 and another call is initiated if necessary.

Assuming the connection is made, in step 506 the Rx refill machine 28 listens to and records a phrase uttered by the IVR.

In step 508, the Rx refill machine 28 converts the recorded utterance into a text string.

In step 510, the Rx refill machine 28 ascertains or classifies the intent of the utterance from the text string by a process referred to as "intent classification".

With intent classification, an intent table is first constructed. The intent table lists a number of "intents". For each intent, one or more of expressions representative of the intent is provided. For a prescription refill IVR tree, the intent of such phrases are typically indicative of (1) a request to clarify if the purpose of the call is to refill a prescription, (2) a request to enter patient identifier information, such as name, date of birth, telephone number, etc., (3) a request to enter a prescription refill number, (4) some indication that the refill request has been successfully made and (5) some indication that the call is complete and the calling party should hang up. For example, if the intent is "enter a refill prescription number", example expressions may be (a) "Enter your prescription number"; (b) "Enter the seven digit prescription number" and (c) "Enter the refill identification number". For each expression in the table, a corresponding Action is provided. The action can be implemented using either machine generated voice (e.g. a verbal response such as a recital of the digits) or the appropriate digits can be entered using dual-tone multi-frequency (DTMF) signaling.

During step 510, the Rx refill machine 28 compares the words in the text string to each of the expressions in the table. Based on the comparison, a probability percentage or score is assigned to each expression entry in the table. The intent of the utterance is then classified from the correspondence having the highest score.

In step 512, the action corresponding to the classified intent is determined from the classification table.

In step 514, the determined action is performed. For example, if the determined action is "Enter 2", then the Rx refill machine 28 recites "2" or generates a DTMF tone indicative of pushing the number 2 on a telephone dial pad. Or of the determined action is enter date of birth, the Rx refill machine 28 recites "Jan. 15, 1948" or the equivalent using DTMF tones.

In step 516, the do action is added to a call ledger.

In decision step 518, it is determined if the action is "hang up". If not, then control is returned to step 506 and the Rx refill machine 28 listens and records the next utterance and the steps 508 through 516 are repeated. By iterating the steps 506 through 516 the IVR is navigated and a call ledger documenting all the actions performed during the call is created.

If the determined action is "hang up", then it is assumed that the refill request was successfully made and the call can terminate. The text string of the utterance indicating that the intent is to hang up may be expressed in a number of ways. For instance, if the utterance includes words like "thank you, "good bye" and/or a date and/or time when the prescription is ready, then the probability will be high that the intent is to hang up.

Referring to FIG. 6, an example "text-to-digit" intent table is illustrated. In this example, one or more expressions are provided for classifying (1) If the purpose of the call is for a prescription refill, (2) Entering the telephone number associated with the patient requesting the refill, (3) entering the prescription number, (4) entering the last name of the patient, (5) confirming the entered last name, (6) asking if additional refills are needed, (7) confirming pickup time, (8) informing patient that no refills are remaining, (9) inform the patient to contact their doctor for additional refills, (10) request for patient to leave a message and (11) hang up because call is over. For each of the expressions, a corresponding Action is listed.

Figure 7:
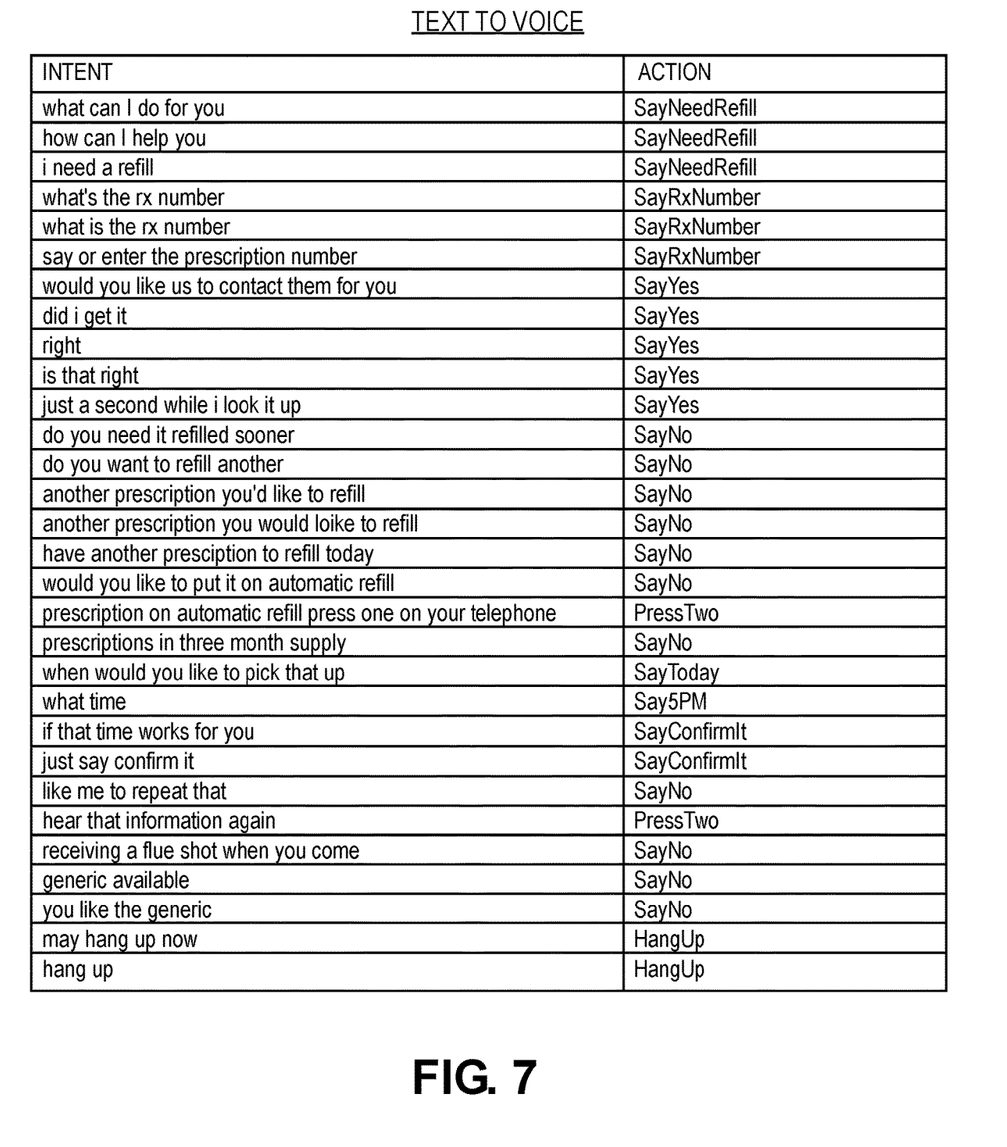

Referring to FIG. 7, an exemplary "text-to-voice" table is illustrated. This table is similar to that above in the sense that multiple expressions for different intents are listed. However, instead of the response being the entering of one or more digits, the Action is entered by machine generated voice.

In various alternative embodiments, an intent table can be implemented in a number of different ways. In one embodiment, an intent table can be constructed for a given patient (e.g., Mary Smith). With a patient-specific table, personal information, such as the name of the patient, date of birth, telephone number, etc. are all maintained in the table and readily available. In an alternative embodiment, the intent table can be a "slotted", meaning instead of including specific data, pointers and/or identifiers are used for retrieving the action information. The use of a slotted table is useful in situations where a single or a reduced set of tables is desired. For example, Walgreen pharmacies may use an IVR that requires the entering of the number "1" to refill a prescription, while the IVR at CVS pharmacies require the entering of the number "2". Rather than using different tables, a slotted table can be used. Depending on which pharmacy chain is being called, either "1" or "2" can be inserted in the slot. In a similar manner, slots for the name of a patient, date of birth, telephone number, etc., can all be included in the table.

The above described process for automating the refilling of a prescription using the Rx refill machine 28 was described in the context of a prescription renewal for a single patient for the sake of simplicity. It should be understood that the Rx refill machine 28 can be used in a similar manner refill the prescription(s) for multiple patients.

Alternative Embodiments

Although only a few embodiments have been described in detail, it should be appreciated that the present application may be implemented in many other forms without departing from the spirit or scope of the disclosure provided herein. Therefore, the present embodiments should be considered illustrative and not restrictive and is not to be limited to the details given herein, but may be modified within the scope and equivalents of the appended claims.

What is claimed is:
1. A method, comprising:
managing a medical prescription fulfillment system for automatically requesting a pharmacy used by a patient to refill a prescription on behalf of the patient, the medical prescription fulfillment system automatically requesting the pharmacy refill the prescription on behalf of the patient by:
receiving medical records pertinent to the patient from a medical insurance provider of the patient;
automatically ascertaining from the medical records pertinent to the patient that the prescription should be refilled in an upcoming time window;
automatically sending a text message to the patient, the text message asking if the patent wishes to have the prescription refilled;
receiving from the patient a reply text message requesting that the prescription be refilled;
automatically directing a machine to initiate a call with an Interactive Voice Response (IVR) tree used by the pharmacy in response to the reply text message from the patient requesting that the prescription be refilled, the machine initiating the call with the IVR tree by using a telephone number associated with a National Provider Identifier (NPI) associated with the pharmacy;

automatically machine navigating the IVR tree, the machine automatically navigating the IVR tree by:
- (a) automatically classifying an intent of an utterance made by the IVR tree;
- (b) automatically ascertaining an action that corresponds to the classified intent;
- (c) automatically performing the action; and
- (d) repeating (a) through (c) such that at least (i) a drug identifier associated with the prescription and (ii) personal information associated with the patient are entered by the machine while navigating the IVR tree;

receiving a notice at the medical prescription fulfillment system that the medical insurance provider has been invoiced for at least a portion of a cost for the prescription;

automatically making a judgment that the request for the refill by the machine navigating the IVR tree was successful based on receiving the notice that the medical insurance provider has been invoiced for at least the portion of the cost for the prescription; and in response to the automatic judgment that the request for the refill was successful, automatically sending a second text message to the patient notifying that the refill for the prescription is or will be available at the pharmacy for pickup.

2. The method of claim 1, wherein automatically classifying the intent of the utterance from the text string further comprises automatically:
- comparing the text string with multiple expressions;
- assigning a probability score for each of the multiple expressions based on the comparison with the text string;
- ascertaining the expression, among the multiple expressions, having the highest probability score; and
- classifying the intent based on the expression having the highest probability score.

3. The method of claim 2, further comprising automatically:
- assigning one of a plurality of intents to each of the multiple expressions respectively; and
- assigning one of several actions to each of the plurality of intents respectively.

4. The method of claim 1, wherein automatically making the judgment that the request for the refill was successful or not from one of the following:
- (a) receiving the notice of that the medical insurance provider has been invoiced for the at least partial payment for the refilling of the prescription;
- (b) ascertaining an intent from machine navigating the IVR tree that the machine should hang up and terminate the call; or
- (c) the entering of (i) the drug identifier associated with the prescription and (ii) the personal information associated with the patient; or
- (d) any combination of (a) through (c).

5. The method of claim 1, further comprising automatically determining that the prescription should be refilled within the upcoming time window at least partially based on an estimation of a supply of the prescription remaining since last filled.

6. The method of claim 1, wherein the records pertinent to the patient include:
- identifier information for the patient;
- a drug ID associated with the prescription;
- refill data for the prescription as prescribed;
- a National Provider Identifier associated with the pharmacy; and
- a history of the patient refilling the prescription.

7. The method of claim 1, wherein the machine automatically navigating the IVR tree further comprises converting the utterance made by the IVR tree into a text string and classifying the intent of the utterance from the text string.

* * * * *